United States Patent
Giese et al.

(10) Patent No.: US 6,765,103 B2
(45) Date of Patent: Jul. 20, 2004

(54) PROCESS FOR THE HYDROGENATION OF UNSATURATED TRANSITION METAL COMPOUNDS

(75) Inventors: Burkhardt Giese, Werne (DE); Richard Lisowsky, Kamen (DE); Jan Timmermann, Dortmund (DE); Thomas Wanke, Werne (DE); Mario Hüttenhofer, Constance (DE)

(73) Assignee: Crompton GmbH, Bergkamen (DE)

( * ) Notice: Subject to any disclaimer, the term of this patent is extended or adjusted under 35 U.S.C. 154(b) by 0 days.

(21) Appl. No.: 10/316,320

(22) Filed: Dec. 11, 2002

(65) Prior Publication Data

US 2003/0109731 A1 Jun. 12, 2003

(30) Foreign Application Priority Data

Dec. 11, 2001 (DE) .......................... 101 60 635

(51) Int. Cl.$^7$ .................... C07F 17/00; B01J 31/00
(52) U.S. Cl. ................ 556/11; 556/12; 556/53; 502/103; 502/117; 526/943
(58) Field of Search ............... 556/11, 12, 53; 526/943; 502/103, 117

(56) References Cited

FOREIGN PATENT DOCUMENTS

DE 2516284 8/1977

OTHER PUBLICATIONS

Von Walter Kaminsky, et al. (1985) "Polymerisation von Propen und Buten mit einem chiralen Zirconocen und Methylaluminoxan als Cokatalysator", Angew. Chem. 97, pp. 507–508.

Dr. Alfred Hothig Verlag, et al. (1987) "Statische und dynamische Schlaufenmischer", Sonderdruck 16, vol. 6, pp. 1–4.

*Primary Examiner*—Porfirio Nazario-Gonzalez
(74) *Attorney, Agent, or Firm*—Scully, Scott, Murphy & Presser

(57) ABSTRACT

The invention relates to a process for preparing transition metal compounds having hydrogenated or partially hydrogenated monocyclic, bicyclic or polycyclic ligands, which is characterized in that the unsaturated monocyclic, bicyclic or polycyclic transition metal compound together with hydrogen is introduced continuously or all at once under pressure into a static mixer in the presence of a suitable solubilizer and a catalyst.

16 Claims, 3 Drawing Sheets

PROCESS FOR THE HYDROGENATION OF UNSATURATED TRANSITION METAL COMPOUNDS

The invention relates to a process for preparing hydrogenated or partially hydrogenated transition metal compounds having monocyclic, bicyclic or polycyclic ligands by hydrogenation of the corresponding unsaturated transition metal compound in a static mixer.

Transition metal compounds are gaining increasing importance as essential constituents of a new generation of catalyst systems for preparing polyolefins ("single site catalysts"). These new catalysts consist, as is known from classical Ziegler-Natta catalysis, essentially of a transition metal compound as catalyst and an alkylaluminoxane as organoaluminium cocatalyst component. As transition metal compound, preference is given to using, for example, cyclopentadienyl, indenyl or fluorenyl derivatives of elements of group IVa of the Periodic Table of the Elements.

The transition metal compounds which can be used according to the invention have monocyclic, bicyclic or polycyclic ligands such as indenyl or fluorenyl, which may be substituted or unsubstituted. The transition metal compounds can be used as alkyl compounds, as halide compounds, as aryl or alkaryl compounds or as alkoxy compounds.

In contrast to conventional Ziegler-Natta catalysts, such systems have a high activity and productivity and are not only capable of controlling the product properties in a targeted manner as a function of the components used and the reaction conditions but also open up a route to hitherto unknown polymer structures having very promising properties with a view to industrial applications. The monocyclic, bicyclic or polycyclic transition metal compounds have a differing polymerization activity and selectivity depending on whether the polycycle is saturated or unsaturated. The hydrogenation and work-up of the transition metal compounds is sometimes technically complicated, the conversions are incomplete, the yields are often low and the products are correspondingly expensive.

Some possible ways of hydrogenating monocyclic, bicyclic or polycyclic transition metal compounds have been described in the literature (W. Kaminsky et al., Angew. Chem. 97 (1985), 507–508).

Some of these processes are technically complicated since they require, inter alia, low reaction temperatures at the beginning or multistage work-up processes and suffer from reduced yields as a result, or the hydrogenated transition metal derivative can often not be obtained in the purity necessary for a high catalyst activity.

It is therefore an object of the present invention to overcome these disadvantages of the prior art and to provide a simple and efficient process for the hydrogenation of monocyclic, bicyclic or polycyclic transition metal compounds.

The invention provides a process for preparing transition metal compounds having hydrogenated or partially hydrogenated monocyclic, bicyclic or polycyclic ligands, which is characterized in that the unsaturated monocyclic, bicyclic or polycyclic transition metal compound together with hydrogen is introduced continuously or all at once under pressure into a static mixer in the presence of a suitable solubilizer and a catalyst. The continuous introduction of hydrogen can also be carried out with return of unreacted hydrogen into the circuit.

Further embodiments of the invention are characterized by the claims.

According to the invention, preference is given to a preparative process in which hydrogen is introduced via a mixing nozzle into a solution or suspension of an unsaturated monocyclic, bicyclic or polycyclic transition metal compound in an aliphatic, cycloaliphatic or aromatic hydrocarbon, if desired a halogenated hydrocarbon, in a static mixer, preferably a flow tube with partial flow return (K. Hübner, Chemie-Technik 6 (1987), 87–92). For the purposes of the present invention, the term solubilizer refers to diluents which lead either to a solution or to a suspension.

The mode of operation of the flow tube with partial flow return (FIG. 1), as is described, for example, in DE-A-25 16 284, is based on a liquid driving jet in an internal tube which transmits momentum to the entire contents of the reactor and thus produces a strong circulation. As a result, the flow of circulated liquid in the reactor is from about 8 to 10 times as high as the volume flow of the driving jet.

In the process of the invention, hydrogen is introduced via the single-component or multicomponent mixing nozzle into a suspension or solution of the unsaturated monocyclic, bicyclic or polycyclic transition metal compound in the reactor in a volume flow ratio of from 1:2000 to 1:40,000, preferably 5000–20,000.

Figure 1:
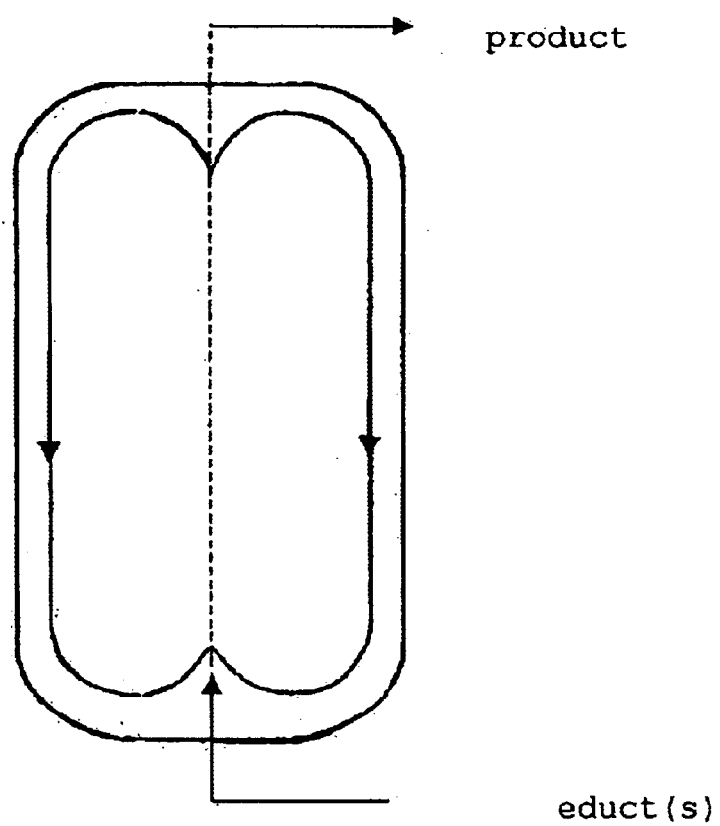
FIG. 1 schematically shows a flow tube with partial flow return.

The flow tube with partial flow return ensures, because of the strong circulation, good and extremely rapid mixing of the abovementioned suspension or solution with the hydrogen (FIG. 1).

The mode of operation of the liquid jet gas compressor (FIG. 2), also known as liquid jet compressor according to the manufacturer GEA (for example), is based on a liquid driving jet which breaks up in a tube after exiting the nozzle and, as a result of the liquid droplets formed, entrains the surrounding gas phase and thus produces a high degree of mixing.

In the process of the invention, the stream of the solution or suspension of the transition metal compound together with the catalyst is pumped with the aid of a pump around a circuit through the liquid jet gas compressor, resulting in the hydrogen being drawn in and mixed in in finely dispersed form.

Figure 2:
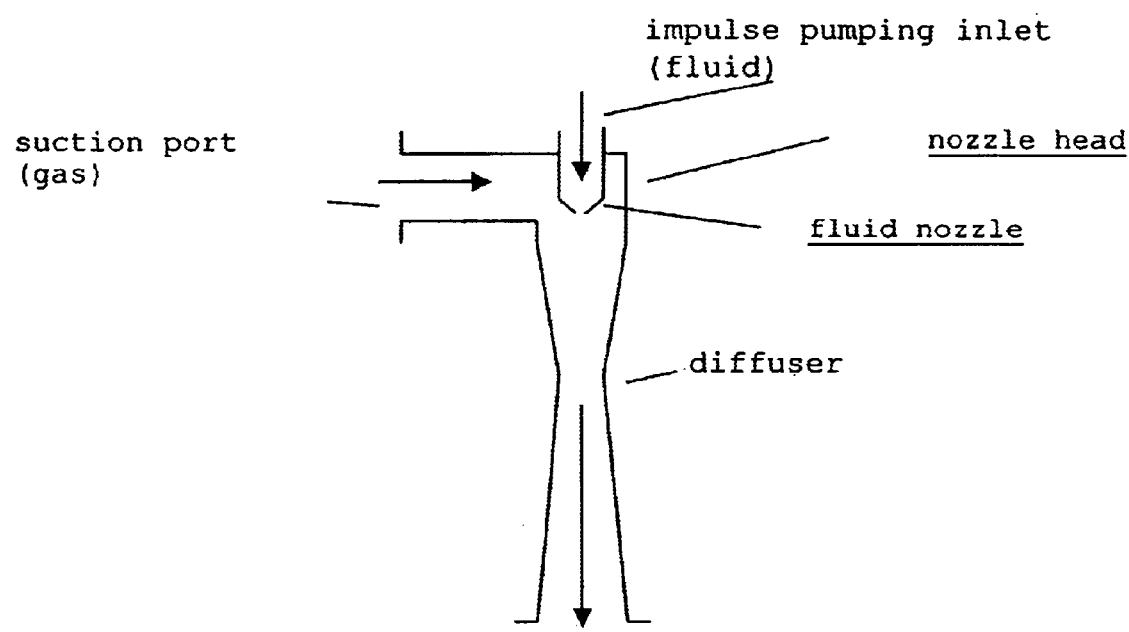
FIG. 2 schematically shows a liquid jet gas compressor.

The liquid jet gas compressor ensures, owing to the strong circulation and the breaking-up of the liquid jet, good and extremely rapid mixing of the abovementioned suspension or solution of the unsaturated monocyclic, bicyclic or polycyclic transition metal compound with the hydrogen (FIG. 2).

The mode of operation of the Venturi mixer (FIG. 3) is based on a tube through which liquid flows and into which the hydrogen gas stream is drawn. As a result of the high flow, the hydrogen is finely dispersed and a high degree of mixing of the gas is thus produced.

In the process of the invention, the stream of solution or suspension of the transition metal compound together with the catalyst is pumped by means of a pump in a circuit through the Venturi mixer, as a result of which the hydrogen is drawn in and mixed in.

Figure 3:
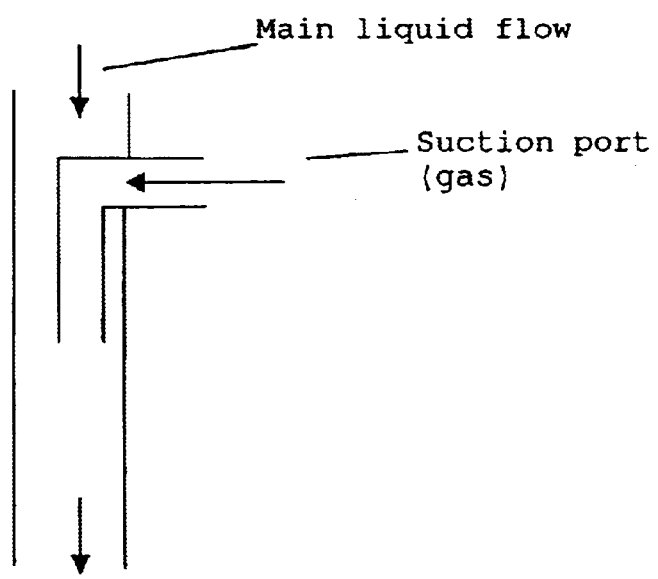
FIG. 3 schematically shows a Venturi mixer.

Owing to the strong circulation and good dispersion of the hydrogen, the Venturi mixer ensures good and extremely rapid mixing of the solution or suspension of the unsaturated monocyclic, bicyclic or polycyclic transition metal compound with the hydrogen (FIG. 3).

The processes of the invention make it possible to prepare hydrogenated or partially hydrogenated transition metal compounds in virtually quantitative yields, without technically complicated process steps. In this context, hydrogenated transition metal compounds are compounds which have no C—C double bond apart from the double bonds in the cyclopentadienyl structure, while partially hydrogenated transition metal compounds are compounds which have at least one C—C double bond in addition to the double bonds in the cyclopentadienyl structure.

In the process of the invention, it is possible to use unsaturated monocyclic, bicyclic or polycyclic transition metal compounds as starting materials.

Preference is given to using indenyl or fluorenyl derivatives of elements of group IVa of the Periodic Table of the Elements as transition metal compounds. The transition metal compounds to be hydrogenated are preferably zirconium, hafnium or titanium complexes.

Particular preference is given to using halides or aryl, alkaryl, alkoxy or alkyl complexes, which may be bridged or unbridged, as unsaturated transition metal compounds. Very particular preference is given to bridged transition metal compounds which are used as halides or alkyl complexes.

Preference is also given, but without implying a restriction, to 1,2-ethylene, Si, Si-dimethylsilyl or 1,1-dimethylmethylene groups being present as bridging units in the transition metal compounds used.

Catalysts used in the process of the invention can be catalysts which are customarily used in hydrogenation, for example Pt, Pd, Ru or Rh catalysts. Preference is given to using a platinum catalyst (as oxide or hydrated oxide, sometimes also supported on support materials such as activated carbon, silica, etc.).

Owing to parameters which can be set in a targeted manner and reproducible process conditions, these hydrogenated or partially hydrogenated monocyclic, bicyclic or polycyclic transition metal compounds prepared by the process of the invention, which are the subject matter of the present invention, have high activities as catalysts and are thus very suitable for the further preparation of catalyst systems for olefin polymerization.

The invention is illustrated below with the aid of examples.

The following examples reflect the general field of application of the present invention and do not imply any restriction.

Percentages are, unless indicated otherwise, percentages by mass.

EXAMPLES

Example 1

Flow Tube with Partial Flow Return

Hydrogenation of 1,2-ethylenebis[indenyl]zirconium dichloride to 1,2-ethylenebis[tetrahydroindenyl]zirconium dichloride by the process of the invention in a flow tube with partial flow return

| | |
|---|---|
| Temperature: | 40° C. |
| Pressure: | 2–3 bar |
| Volume flow of $H_2$: | 600–700 [standard 1/h] |
| Reaction time: | 46 min |
| Materials used: | 5 kg of dichloromethane |
| | 250 g of transition metal compound |
| | 5 g of $PtO_2.H_2O$ |
| Conversion after 46 min (NMR): | >98% |

Procedure:

Dichloromethane, platinum oxide hydrate and transition metal compound were placed in the reactor to form a suspension and heated to 40° C. After starting up the circulation pump, hydrogen was introduced into the flow tube with partial flow return via the metering nozzle. The conversion can be followed by NMR spectroscopy on samples taken during the course of the reaction.

Example 2

Liquid Jet Gas Compressor

Hydrogenation of 1,2-ethylenebis[indenyl]zirconium dichloride to 1,2-ethylenebis[tetrahydroindenyl]zirconium dichloride by the process of the invention in a liquid jet gas compressor

| | |
|---|---|
| Temperature: | 40° C. |
| Pressure: | 2–3 bar |
| Volume flow of $H_2$: | Single introduction |
| Reaction time: | 210 min |
| Materials used: | 5 kg of dichloromethane |
| | 50 g of transition metal compound |
| | 5 g of $PtO.2H_2O$ |
| Conversion (NMR) after 210 min: | >98% |

Procedure:

Dichloromethane, platinum oxide hydrate and transition metal compound were placed in the reactor and heated to 40° C. After starting up the circulation pump, hydrogen was injected. The conversion can be followed by NMR spectroscopy on samples taken during the course of the reaction.

Example 3

Venturi Mixer

Hydrogenation of 1,2-ethylenebis[indenyl]zirconium dichloride to 1,2-ethylenebis[tetrahydroindenyl]zirconium dichloride by the process of the invention in a Venturi mixer

| | |
|---|---|
| Temperature: | 40° C. |
| Pressure: | 2–4 bar |
| Volume flow of $H_2$: | Single introduction |
| Reaction time: | 100 min |
| Materials used: | 5 kg of dichloromethane |
| | 50 g of transition metal compound |
| | 5 g of $PtO_2.H_2O$ |
| Conversion (NMR) after 100 min: | 98% |

Procedure:

Dichloromethane, platinum oxide hydrate and transition metal compound were placed in the reactor and heated to 40° C. After starting up the circulation pump, hydrogen was injected. The conversion can be followed by NMR spectroscopy on samples taken during the course of the reaction.

Comparative Example 1

Autoclave

Hydrogenation of 1,2-ethylenebis[indenyl]zirconium dichloride to 1,2-ethylenebis[tetrahydroindenyl]zirconium dichloride in a classical pressure reactor (autoclave)

| | |
|---|---|
| Temperature: | 50° C. |
| Pressure: | 100 bar |
| Reaction time: | 1 day |
| Materials used: | 50 g of dichloromethane |

|       |                                    |
|-------|------------------------------------|
|       | 2.5 g of transition metal compound |
|       | 0.050 g of PtO$_2$.H$_2$O          |
|       | 0.050 g of CaH$_2$                 |
| Yield:| <76%                               |

Procedure:

Prehydrogenation of the catalyst was carried out by weighing the catalyst and part of the dichloromethane into the autoclave and prehydrogenating the catalyst by means of hydrogen at 10 bar. After purging the autoclave a number of times with nitrogen, the transition metal compound and the remaining dichloromethane are then added. The hydrogenation is carried out at 50° C. and 100 bar for 4 hours. Monitoring of the reaction by means of samples taken during the reaction is not possible.

What is claimed is:

1. Process for preparing transition metal compounds having hydrogenated or partially hydrogenated monocyclic, bicyclic or polycyclic ligands, characterized in that the unsaturated monocyclic, bicyclic or polycyclic transition metal compound and hydrogen are introduced into a static mixer in the presence of a suitable solubilizer and a catalyst.

2. Process according to claim 1 characterized in that the ligand or ligands to be hydrogenated on the transition metal compound are indenyl or fluorenyl derivatives.

3. Process according to claim 1 or 2, characterized in that the transition metal compounds used are halides or aryl, alkaryl, alkoxy or alkyl complexes.

4. Process according to any claim 3, characterized in that bridged transition metal compounds are used as halides or alkyl complexes.

5. Process according to claim 4, characterized in that 1,2-ethylene, Si, Si-dimethylsilyl, isopropyl or 1,1-dimethylmethylene groups are present as bridging units in the transition metal compounds used.

6. Process according to claim 1, characterized in that the hydrogen can be introduced all at once, continuously or in recirculated form.

7. Process according to any to claim 1, characterized in that the static mixer used is a flow tube with coaxial partial flow return, a liquid jet gas compressor or a Venturi mixer.

8. Process according to any claim 1, characterized in that the transition metal compound to be hydrogenated can be used as solution or as suspension in a suitable solubilizer.

9. Process according to claim 1 or 8 characterized in that a hydrocarbon or a halogenated hydrocarbon is used as solubilizer.

10. Process according to claim 1, characterized in that the catalyst used is a Pt, Pd, Ru or Rh hydrogenation catalyst.

11. Process according to claim 1 or 2, characterized in that the transition metal compounds to be hydrogenated are zirconium, hafnium or titanium complexes.

12. Process according to claim 1, characterized in that the transition metal compounds to be hydrogenated are bridged bisindenyl transition metal compounds containing zirconium, hafnium or titanium as transition metal and a 1,2-ethylene, Si, Si-dimethylsilyl, isopropyl or 1,1-dimethylmethylene group as bridging unit.

13. Process according to claim 3, characterized in that the transition metal compounds to be hydrogenated are zirconium, hafnium or titanium complexes.

14. Process according to claim 4, characterized in that the transition metal compounds to be hydrogenated are zirconium, hafnium or titanium complexes.

15. Process according to claim 5, characterized in that the transition metal compounds to be hydrogenated are zirconium, hafnium or titanium complexes.

16. Process according to claim 4, characterized in that the transition metal compounds to be hydrogenated are bridged bisindenyl transition metal compounds containing zirconium, hafnium or titanium as transition metal and a 1,2-ethylene, Si, Si-dimethyllsilyl, isopropyl or 1,1-dimethylmethylene group as bridging unit.

* * * * *